United States Patent [19]

Leuschen et al.

[11] Patent Number: 5,368,160
[45] Date of Patent: Nov. 29, 1994

[54] STERILE PACKAGING FOR DENTAL IMPLANT SYSTEM

[75] Inventors: Jeffrey D. Leuschen, Carlsbad, Calif.; Donald E. Hendricks, Austin, Tex.

[73] Assignee: Calcitek, Inc., Carlsbad, Calif.

[21] Appl. No.: 171,003

[22] Filed: Dec. 21, 1993

[51] Int. Cl.$^5$ ............................................... A61C 8/00
[52] U.S. Cl. .................................... 206/339; 206/63.5; 433/174
[58] Field of Search ............... 206/338, 339, 363, 438, 206/63.5; 433/173, 174, 201.1

[56] References Cited

U.S. PATENT DOCUMENTS

| | | | |
|---|---|---|---|
| 4,758,161 | 7/1988 | Niznick | 433/201.1 X |
| 5,197,881 | 3/1993 | Chalifoux | 433/173 |
| 5,209,659 | 5/1993 | Friedman et al. | 433/174 X |
| 5,281,140 | 1/1994 | Niznick | 433/173 X |
| 5,312,254 | 5/1994 | Rosenlicht | 433/174 X |

OTHER PUBLICATIONS

"Surgical Instructions", Steri-Oss, Inc.

*Primary Examiner*—Jacob K. Ackun, Jr.
*Attorney, Agent, or Firm*—John R. Merkling

[57] ABSTRACT

A sterile delivery system for a dental implant comprising a vial and cap with a detachable driver. The dental implant is secured to the driver by a screw. Once the implant has been secured in the jaw of a patient, the driver is removed and the screw is replaced on the implant root portion as a healing screw. In this fashion, the total number of parts required, and the number of parts contacting the implant are reduced, thus reducing the possibility of infection and simplifying the number of components in the sterile delivery system.

11 Claims, 2 Drawing Sheets

STERILE PACKAGING FOR DENTAL IMPLANT SYSTEM

FIELD OF OUR INVENTION

Our invention relates to sterile packaging for dental implants.

BACKGROUND OF THE INVENTION

Successful dental implants date from about 1968, when a biocompatible metal blade was fitted into a prepared site in a patient's jaw. The blade itself was perforated or vented to allow bone and blood vessels to reunite readily. A projecting metal head, either unitary with or detachable from the blade, provided an anchor for attachment of a fixed bridge. Another endosseous metal implant design is the basket type, having a projecting metal head. This implant is used for partial support of a fixed bridge.

There are at present a number of different dental implant systems in use. Most systems include an artificial root portion or implant cylinder which is placed into a custom bored hole in the jaw bone. A prosthetic coronal section is attached to the artificial root portion when healing and bone integration of the artificial root portion is complete, and a dental prosthetic appliance, such as a crown, denture, partial denture or bridge, is attached to the coronal section. The prosthetic coronal section must pass through the connective tissue and overlying mucosa to attach to the prosthesis.

Since dental implants are to be implanted in the jaw of a patient, it is important that the implants be maintained in a sterile condition, so far as possible. Moreover, it is necessary for the implants to heal in place. This usually involves placing the artificial root portion in the jaw and covering the proximal end with a healing screw, closing the mucosa over the screw and allowing healing to proceed. Thereafter, the healing screw and root portion are again exposed, the healing screw is removed, and the coronal section and dental prosthetic appliance attached. It is important, therefore, that both the healing screw, and the root portion be maintained in as sterile condition as possible.

SUMMARY OF OUR INVENTION

With the foregoing in mind, we have invented a sterile delivery system for a dental implant comprising a vial and cap with a detachable driver. The dental implant is secured to the driver by a screw. Once the implant has been secured in the jaw of a patient, the driver is removed and the same screw is replaced on the implant root portion as a healing screw. In this fashion, the total number of parts required, and the number of pans contacting the implant are reduced, thus reducing the possibility of infection and simplifying the number of components in a sterile delivery system.

It is, therefore, the object of our invention to provide a sterile delivery system for a dental implant having a reduced number of total pans necessary for implanting the root portion of the implant.

It is also the object of our invention to provide such a system wherein a healing screw serves both as part of the sterile delivery system and as a healing screw.

These and other objects and features of our invention we will become apparent from the following detail description of our preferred embodiment, taken in connection with the accompanying drawings.

BRIEF DESCRIPTION OF THE DRAWINGS

FIG. I is a plan view, in partial cross-section, of a sterile package for a dental implant, according to our invention.

DETAILED DESCRIPTION OF THE PREFERRED EMBODIMENT

We will now describe our preferred embodiment, with reference to the accompanying drawings. Like numerals will be used to designate like parts throughout.

Figures 1, 4:
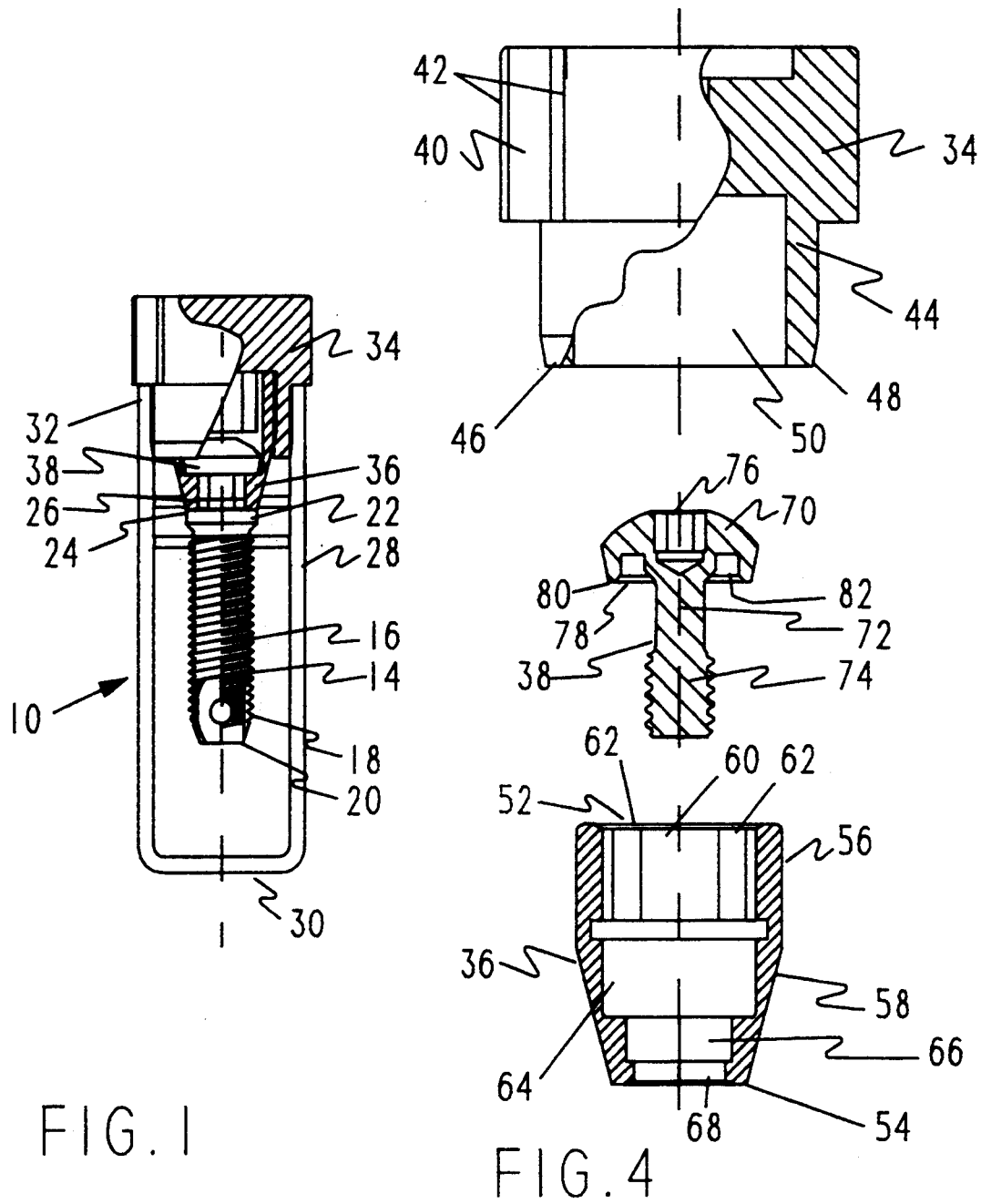
FIG. 4 is a partial cross-section of the portion of the system shown in FIG. 2, taken along line 4—4 in FIG. 2.
Figure 2:
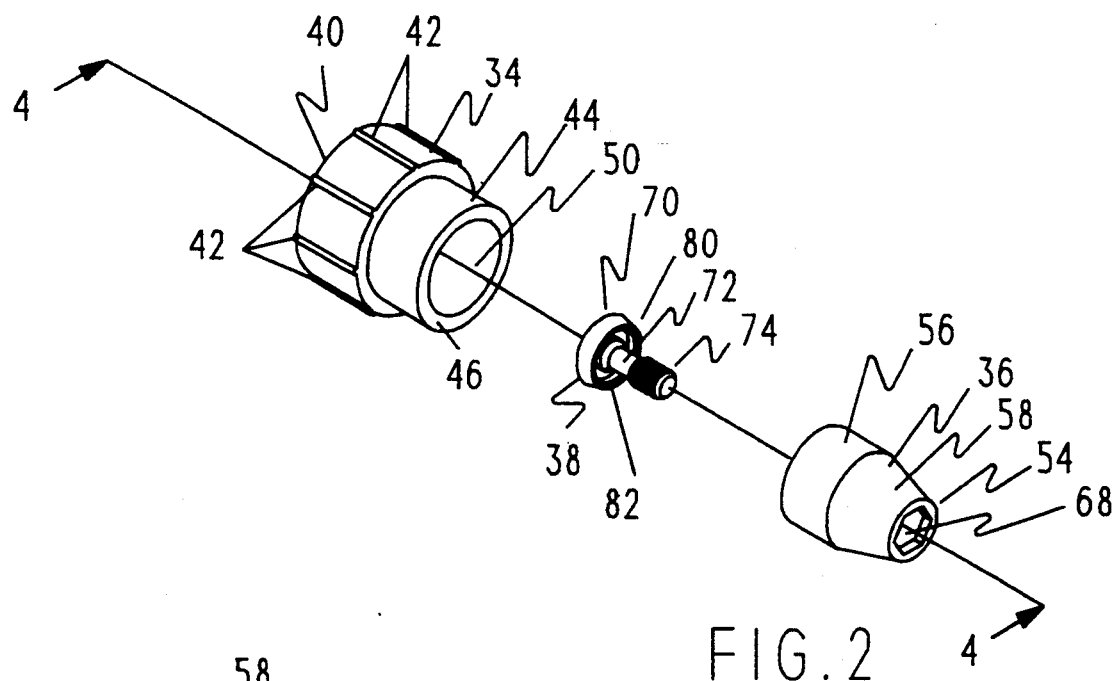
FIG. 2 is an perspective view of a portion of the system of FIG. 1.
Figure 3:
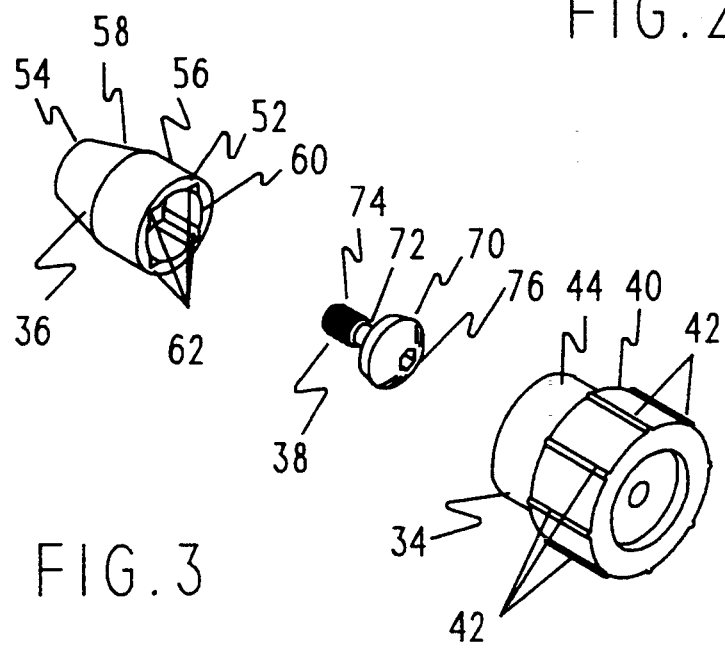
FIG. 3 is a reverse perspective view of the portion of the system shown in FIG. 2.

FIG. 1 shows a sterile delivery system generally designated 10 according to our invention, together with a root portion 14 for a dental implant. We have illustrated the root portion 14 in a form similar to the well-known Branemark implants, marketed by Nobelpharma. Similar implants are available from several manufacturers. As is well-known in this art, such an implant comprises a threaded shaft 16 having a self-taping feature 18 at a distal end 20 thereof. At a proximal end 22 there is usually a lip 24 and a raised hexagonal nut 26. In the center of the nut and concentric with the dental implant 14, there is a threaded internal bore, which is not shown. As is known in this art, the threaded bore is used to secure a coronal section to the implant root 14 after implantation has been accomplished.

The sterile packaging 10 comprises a vial 28 which generally encloses the root portion 14. The vial 28 has a closed end 30 and an open end 32. The open end 32 is generally sealed by a cap 34 which supports a driver 36. The root portion of the implant 14 is secured to the driver 36 by a healing screw 38. The cap 34 has a generally cylindrical upper surface 40 with circumferential parallel ridges 42. The ridges 42 make it easier to grasp the cap and twist it, driving the implant into the jaw bone, as will be more fully described hereafter. Distal from the cylindrical surface 40 is a socket section 44 which fits into the open end 32 of the vial 28, sealing the vial. A distal edge 46 of the socket section 44 has a circumferential chamfer 48 which makes it easier to assemble the cap and vial. A cavity 50 within the socket section 44 opens distally to receive the driver 36. The driver 36 has a proximal end 52 which is received within the cavity 50 and a distal end 54 which abuts the dental implant 14. Near the proximal end 52 is a cylindrical outer surface 56 which fits with a interference fit within the cavity 50. A frusto-conical taper 58 extends from the cylindrical outer surface 56 to the distal end 54. Within the driver 36, and adjacent the proximal end 52, there is a cylindrical cavity 60 with four longitudinal grooves 62 placed circumferentially around the cavity 60. The grooves 62 receive a square wrench, as will be more particularly described below. Distal from the cylindrical cavity 60, is an inner chamber 64 and distal therefrom is a bore 66. Adjacent the distal end 54 and connecting the distal end to the bore 66 is an internal hexagonal passage 68 which receives and engages the external hexagonal nut 26 on the implant 14.

The final element of our system is the healing screw 38. As seen in FIG. 4, the healing screw 38 comprises a screw head 70 and a shaft 72. The shaft 72 has a distal threaded portion 74 which engages the threaded internal bore of the implant, as described above. In our preferred embodiment, the healing screw 38 has an internal hexagonal feature 76 for driving the screw. On a distal side 78 of the screw head 70, there is a circumferential lip 80 which forms a groove 82. When used as a healing screw, the screw 38 will fit down onto the proximal end of the implant 14 and the lip 80 will fit over the external hexagonal nut 26.

To install the implant 14 into a patient's jaw, an implantation site is prepared in a conventional manner. When the site is prepared, the cap 34 is removed from the vial, carrying with it both the driver 36 and implant 14 secured by the healing screw 38. Using finger pressure, the implant is threaded into the implantation site by gently twisting the cap. This process continues until the resistive torque becomes high enough so that the cap twists on the driver 36. The cap 34 is then removed from the driver. The implant can then be more completely installed by engaging the driver 36 with a square drive wrench inserted into the cylindrical cavity 6 and engaging the internal grooves 62. Preferably, this square drive wrench would have a ratchet feature. When the implant has been completely seated within the implant site, a hex wrench is used to unscrew the healing screw 38 and the driver 36 is removed. The healing screw is reassembled onto the implant where it covers the external hexagonal feature 26 on the implant. The mucosa is then closed over the implant in a conventional manner so that healing can take place.

Our invention may be embodied in other specific forms without departing from the spirit or essential characteristics thereof. The present description is considered in all respects to be illustrative and not restrictive, the scope of our invention being indicated by the appended claims rather than the foregoing description and all changes which come within the meaning and range of equivalency of the claims are therefore intended to be embraced therein.

We claim as our invention:

1. A package for a root portion of a dental implant, said package comprising
   a vial;
   a cap for closing said vial;
   driver means releasibly connected to said cap for supporting said root portion; and
   means for connecting said root portion to said driver means and for providing a healing surface covering a proximal end of said root portion during initial healing associated with implanting said root portion in a patient's jaw.

2. The package according to claim 1 wherein said means for connecting and for providing a healing surface comprises a screw.

3. The package according to claim 2 wherein said screw comprises a head and a threaded shaft, said head having a proximal side and a distal side and a wrench-engaging feature on said proximal side thereof and a circumferential groove on said distal side thereof.

4. The package according to claim 3 wherein said groove is sized to receive a raised wrench-engaging feature on said root portion.

5. The package according to claim 4 wherein said driver means comprises a distal end for supporting said root portion and a proximal end spaced away from said distal end, said proximal end having a wrench-engaging feature.

6. The package according to claim 5 wherein said driver wrench-engaging feature comprises a cylindrical cavity having circumferentially spaced parallel longitudinal grooves.

7. The package according to claim 6 wherein said cap has a cylindrical cavity and wherein said driver has a cylindrical outer surface, said surface fitting within said cavity.

8. The package according to claim 1 wherein said driver means comprises a distal end for supporting said root portion and a proximal end spaced away from said distal end, said proximal end having a wrench-engaging feature.

9. The package according to claim 8 wherein said driver wrench-engaging feature comprises a cylindrical cavity having circumferentially spaced parallel longitudinal grooves.

10. The package according to claim 9 wherein said cap has a cylindrical cavity and wherein said driver has a cylindrical outer surface, said surface fitting within said cavity.

11. The package according to claim 1 wherein said cap has a cylindrical cavity and wherein said driver has a cylindrical outer surface, said surface fitting within said cavity.

* * * * *